US009557341B2

(12) United States Patent
Sungkanuparph et al.

(10) Patent No.: US 9,557,341 B2
(45) Date of Patent: Jan. 31, 2017

(54) RISK ASSESSMENT FOR CUTANEOUS ADVERSE DRUG REACTIONS FROM ANTIRETROVIRAL AGENT

(75) Inventors: Somnuek Sungkanuparph, Bangkok (TH); Sasisopin Kiertiburanakul, Bangkok (TH); Thanyachai Sura, Bangkok (TH); Wasun Chantratita, Bangkok (TH); Soranun Chantarangsu, Bangkok (TH); Angkana Charoenyingwattana, Bangkok (TH); Surakameth Mahasirimongkol, Nonthaburi (TH); Michiaki Kubo, Yokohama (JP); Taisei Mushiroda, Yokohama (JP); Yusuke Nakamura, Yokohama (JP)

(73) Assignees: MAHIDOL UNIVERSITY, Salaya, Nakhon (TH); RIKEN, Saitama (JP); DEPARTMENT OF MEDICAL SCIENCES, MINISTRY OF PUBLIC, Nonthaburi (TH); THAILAND CENTER OF EXCELLENCE FOR LIFE SCIENCES (OKMD), Bangkok (TH)

(*) Notice: Subject to any disclaimer, the term of this patent is extended or adjusted under 35 U.S.C. 154(b) by 403 days.

(21) Appl. No.: 13/133,520

(22) PCT Filed: Dec. 11, 2009

(86) PCT No.: PCT/JP2009/071070
§ 371 (c)(1),
(2), (4) Date: Aug. 23, 2011

(87) PCT Pub. No.: WO2010/067900
PCT Pub. Date: Jun. 17, 2010

(65) Prior Publication Data
US 2011/0301043 A1    Dec. 8, 2011

(30) Foreign Application Priority Data
Dec. 12, 2008    (TH) .............................. 0801006378

(51) Int. Cl.
*C12Q 1/68*        (2006.01)
*G01N 33/94*    (2006.01)
*G01N 33/68*    (2006.01)

(52) U.S. Cl.
CPC .......... *G01N 33/6893* (2013.01); *G01N 33/94* (2013.01); *G01N 33/9493* (2013.01);
(Continued)

(58) Field of Classification Search
None
See application file for complete search history.

(56) References Cited

U.S. PATENT DOCUMENTS

2003/0165884 A1    9/2003  Chow

OTHER PUBLICATIONS

Lesueur, F. et al. PLoS ONE 9:e906 (Sep. 2007).*
(Continued)

*Primary Examiner* — Diana B Johannsen
(74) *Attorney, Agent, or Firm* — Casimir Jones, SC

(57) ABSTRACT

The present invention provides a method of predicting the risk of a patient for developing cutaneous adverse drug reaction to non-nucleoside reverse transcriptase inhibitors such as nevirapine by using HLA-B*3505 allele and/or polymorphisms in the CCHCR1 gene.

4 Claims, 4 Drawing Sheets

(52) U.S. Cl.
CPC ..... *C12Q 1/6883* (2013.01); *C12Q 2600/106* (2013.01); *C12Q 2600/156* (2013.01); *G01N 2800/20* (2013.01); *G01N 2800/50* (2013.01)

(56) References Cited

OTHER PUBLICATIONS

Lesueur, F. et al PLos ONE 9:e906, Supplementary Table S4 (1 page) (Sep. 2007).*
Leal, L. et al. Actas Dermosifiliogr. 99:753 (2008).*
"Division of AIDS Table for Grading the Severity of Adult and Pediatric Adverse Events," URL <www3.niaid.nih.gov/research/resources/DAIDSClinRsrch/PDF/Safety/DAIDSAEGradingTable.pdf>, version 1.0, pp. 1-20 (Dec. 28, 2004).
Abel, Sylvie, et al., "Abacavir Hypersensitivity," The New England Journal of Medicine, 358, No. 23, pp. 2514-2516 (Jun. 5, 2008).
Al-Hedaithy, Mogbil A., et al., "Hypersensitivity Anaphylactoid Reaction to Pefloxacin in a Patient With AIDS," The Annals of Pharmacotherapy, 30, No. 6, pp. 612-614 (Jun. 1996).
Baylor, Melisse Sloas, et al., "Hepatotoxicity Associated With Nevirapine Use," J Acquir Immune Defic Syndr, vol. 35, No. 5, pp. P538-P539 (Apr. 15, 2004).
Bureau of Epidemiology, Department of Disease Control, Ministry of Public Health, "Status of Thailand AIDS epidemic, End of Jul. 31, 2010," www.epid.moph.go.th (2010), (4 pages).
De Maat, Monique M.R., et al., "Incidence and risk factors for nevirapine-associated rash," Eur J Clin Pharmacol (2003) 59: pp. 457-462 (Aug. 12, 2003).
DHHS Panel on Antiretroviral Guidelines for Adults and Adolescents, "Guidelines for the Use of Antiretroviral Agents in HIV-1-Infected Adults and Adolescents," URL http://www.aidsinfo.nih.gov/ContentFiles/AdultandAdolescentGL.pdf. (Jan. 29, 2008), (134 pages).
English Translation of International Search Report mailed Mar. 23, 2010 from International Patent Application No. PCT/JP2009/071070, (2 pages).
Gangar, Mona, et al., "Frequency of cutaneous reactions on rechallenge with Nevirapine and Delavirdine," The Annals of Pharmacotherpy, 34, 7/8, pp. 839-842 (Jul./Aug. 2000).
Hetherington, Seth, et al., "Genetic variations in HLA-B region and hypersensitivity reactions to abacavir," The Lancet, vol. 359, 9312, pp. 1121-1122 (Mar. 30, 2002).
Hung, Shuen-Iu, et al., "HLA-B*5801 allele as a genetic marker for severe cutaneous adverse reactions caused by allopurinol," PNAS, vol. 102, No. 11, pp. 4134-4139 (Mar. 15, 2005).
Kiertiburanakul, Sasisopin, et al., "Risk Factors for Nevirapine-Associated Rash Among HIV-Infected Patients with Low CD4 Cell Counts in Resource-Limited Settings," Current HIV Research, 6, pp. 65-69 (2008).
Lazarou, Jason, et al., "Incidence of Adverse Drug Reactions in Hospitalized Patients: A Meta-analysis of Prospective Studies," JAMA, 279, No. 15, pp. 1200-1205 (Apr. 15, 1998).
Lee, M. P., et al., "Tolerability and toxicity of non-nucleoside reverse transcriptase inhibitors (NNRTI) in a Chinese predominant cohort," The XV International AIDS Conference Abstract No. WePeB5873 (2004).
Mallal, S., et al., "Association between presence of HLA-B*5701, HLA-DR7, and HLA-DQ3 and hypersensitivity to HIV-1 reverse-transcriptase inhibitor abacavir," The Lancet, vol. 359, 9308, pp. 727-732 (Mar. 2, 2002).
Martin, Annalise M., et al., "Predisposition to abacavir hypersensitivity conferred by HLA-B*5701 and a haplotypic Hsp70-Hom variant," PNAS, vol. 101, No. 12, pp. 4180-4185 (Mar. 23, 2004).
Martin, Annalise M., et al., Predisposition to nevirapine hypersensitivity associated with HLA-DRB1*0101 and abrogated by low CD4 T-cell counts, AIDS, 19, No. 1, pp. 97-99 (Jan. 3, 2005).
Mehta, Ushma, et al., "Is it safe to switch between efavirenz and nevirapine in the event of toxicity?" Lancet Infect Dis, vol. 7, No. 11, pp. 733-738 (Nov. 2007).
Pirmohamed, Munir, et al., "Adverse drug reactions as cause of admission to hospital: prosective analysis of 18 820 patients," BMJ, vol. 329, 7456, pp. 15-19 (Jul. 3, 2004).
Raviglione, Mario C., et al., "Clinical Features and Management of Severe Dermatological Reactions to Drugs," Drug Safety 5, No. 1, pp. 39-64 (1990).
Sanne, Ian, et al., "Severe Hepatotoxicity Associated with Nevirapine Use in HIV-Infected Subjects," J Infect Dis, 191, No. 6, pp. 825-829 (Mar. 15, 2005).
Soranun, C., et al., "HLA-B*3505 allele is a strong predictor for nevirapine-induced skin adverse drug reactions in Thai HIV-infected patients," The Abstracts of the 53rd annual meeting of the Japan Society of Human Genetics, 53, p. 180 (Oct. 17, 2008).
Tojo, Yuriko, et al., "Development of an Automation System for Single Nucleotide Polymorphisms Genotyping Using Bio-Strand, a New Three-Dimensional Microarray," Journal of Bioscience and Bioengineering, vol. 99, No. 2, pp. 120-124 (2005).
Uetrecht, Jack, "Idiosyncratic Drug Reactions: Predicting the Unpredictable," The Journal of Toxicological Sciences, vol. 29, No. 4, p. 291 S6-5 (Oct. 2004).
UNAIDS, "AIDS epidemic update," WHO (Dec. 2007), (60 pages).
Yamamoto, Yoshihiko, et al., "Leukocytopenia due to Zidovudine-and Nevirapine-Containing Regimens in Elderly Patients with HIV Infection," Jpn. J. Infect. Dis., 53, No. 6, pp. 244-245 (Dec. 2000).
Zucman, David, et al., "Prospective Screening for Human Leukocyte Antigen-B*5701 Avoids Abacavir Hypersensitivity Reaction in the Ethnically Mixed French HIV Population," J Acquir Immune Defic Syndr, vol. 45, No. 1, pp. 1-3 (May 1, 2007).
Office Action dated Dec. 20, 2012 from Singapore Patent Application No. 201104243-9, (10 pages).
Cano, Pedro, et al., "Common and Well-Documented HLA Alleles," Report of Ad-Hoc Committee of the American Society for Histocompatibility Immunogenetics, Human Immunology, 68, 392-417 (2007).

* cited by examiner

_US 9,557,341 B2_

RISK ASSESSMENT FOR CUTANEOUS ADVERSE DRUG REACTIONS FROM ANTIRETROVIRAL AGENT

CROSS REFERENCE TO RELATED APPLICATIONS

The present application is a Section 371 U.S. national stage entry of pending International Patent Application No. PCT/JP2009/071070, International Filing Date Dec. 11, 2009, which published on Jun. 17, 2010 as Publication No. WO 2010/067900, which claims the benefit of Thailand Patent Application No. 0801006378, filed Dec. 12, 2008, the contents of which are incorporated by reference in their entireties.

TECHNICAL FIELD

The present invention relates generally to the field of identification of patients who are susceptible to cutaneous adverse drug reaction to the non-nucleoside HIV reverse transcriptase inhibitor, nevirapine. In particular, the invention provides method(s) for detecting patients who should avoid the use of nevirapine because they are in a high risk category for nevirapine-induced cutaneous adverse drug reaction.

REFERENCES www3.niaid.nih.gov/research/resources/DAIDSClinRsrch/PDF/Safety/DAIDSAEGradingTable.pdf Lazarou J., et al (1998). Incidence of adverse drug reactions in hospitalized patients: a meta-analysis of prospective studies. Jama. 279 (15):1200-1205

Pirmohamed M., et al (2004). Adverse drug reactions as cause of admission to hospital: prospective analysis of 18 820 patients. Bmj. 329(7456): 15-19

Raviglione M. C., et al (1990). Clinical features and management of severe dermatological reactions to drugs. Drug Saf. 5(1):39-64

Hung S. I., et al (2005). HLA-B*5801 allele as a genetic marker for severe cutaneous adverse reactions caused by allopurinol. Proc Natl Acad Sci USA. 102(11):4134-4139

Abel S., et al (2008). Abacavir hypersensitivity. N Engl J Med 2008; 358(23): 2514-16.

Kiertiburanakul S., et al (2008). Risk factors for nevirapine-associated rash among HIV-infected patients with low CD4 cell counts in resource-limited settings. Curr HIV Res. 6(1):65-69

Zucman D., et al (2007). Prospective screening for human leukocyte antigen-B*5701 avoids abacavir hypersensitivity reaction in the ethnically mixed French HIV population. J Acquir Immune Defic Syndr. 45(1):1-3

UNAID/WHO, 2007 www.epid.moph.go.th (aidinfo.nih.gov/ContentFiles/AdultandAldolescentGL.pdf) de Maat M M, et al (2003),Incidence and risk factors for nevirapine-associated rash. Eur J Clin Pharmacol. 2003 September; 59(5-6):457-62.

Mehta U., et al (2007). Is it safe to switch between efavirenz and nevirapine in the event of toxicity?. Lancet Infect Dis 7(11): 733-8.

Sanne I, et al, (2005). Severe hepatotoxicity associated with nevirapine use in HIV-infected subjects. J Infect Dis. March 15; 191(6):825-9.

Mallal, S., D. Nolan, et al. (2002). Association between presence of HLA-B*5701, HLA-DR7, and HLA-DQ3 and hypersensitivity to HIV-1 reverse-transcriptase inhibitor abacavir. Lancet 359(9308): 727-32.

Hetherington, S., A et al. (2002). Genetic variations in HLA-B region and hypersensitivity reactions to abacavir. Lancet 359(9312): 1121-2.

Martin, A. M., et al. (2004). Predisposition to abacavir hypersensitivity conferred by HLA-B*5701 and a haplotypic Hsp70-Hom variant." Proc Natl Acad Sci USA 101(12): 4180-5.

Martin A M, et al (2005). Predisposition to nevirapine hypersensitivity associated with HLA-DRB1*0101 and abrogated by low CD4 T-cell counts. AIDS. January 3; 19(1):97-9.

All of the publications cited above or elsewhere in this application are herein incorporated by reference in their entirely to the same extent as if the disclosure of each individual publication was specifically and individually indicated to be incorporated by reference in its entirely.

BACKGROUND ART

Adverse drug reactions occur during the drug development process and post-marketing of the prescribe-based medicine. They are responsible for the termination of approximately 20% of investigational new drugs in the pharmaceutical pipeline. About 1% of marketed drugs is withdrawn or restricted post-marketing due to safety-related issues.

During 1994, adverse drug reactions affected over 2 million people in the United States, resulting in over 100,000 deaths (Lazarou et al., JAMA 1998).

In 2002, adverse drug reactions accounted for 6.5% of hospital admissions and 0.15% of subsequent deaths in the United Kingdom (Pirmohamed et al., BMJ 2004).

Cutaneous adverse drug reactions are among the most common adverse drug reactions and may caused by immune or non-immune mechanisms. The severities of cutaneous reactions were graded according to Division of AIDs table for grading the severities of adverse events NIAID/NIH. Briefly, grade 1: localized macular rash; grade 2: diffuse macular, maculopapular or morbilliform rash or target lesions; grade 3: diffuse macular, maculopapular or morbilliform rash with vesicle or limited number of bullae or superficial ulceration of mucous membrane limited to one site; and grade 4: extensive or generalized bullous lesions or Stevens-Johnson syndrome (SJS) or ulceration of mucous membrane involving two or more distinct mucosal sites or toxic epidermal necrolysis (TEN). (www3.niaid.nih.gov/research/resources/DAIDSClinRsrch/PDF/Safety/DAIDSAEGradingTable.pdf)

Risk factors for the development of cutaneous adverse drug reaction may be related to the host factors (eg. certain HLA alleles), the drug and its metabolites (e.g. its reactivity), and underlying conditions (e.g. viral infections). Antibiotics, nonsteroidal anti-inflammation agents, anticonvulsant drugs (Raviglione et al., Drug Saf 1990), allopurinol (Hung et al., Proc Natl Acad Sci USA 2005), antiretroviral agents, particularly abacavir (Abel et al., N Engl J Med 2008) and nevirapine (Kiertiburanakul et al., Curr HIV res 2008), are among the most common causative agents.

Pharmacognomics is the study of biomarkers variations such as genetic variation, RNA variations, protein variations or combination of these variation in the response to medications. The development of pharmacogenomics has implied that the susceptibility to adverse drug reactions is associated with genetic variants. A successful example of the application of pharmacogenomic study to prevent hypersensitivity syndromes is genotyping of HLA-B*5701 before prescribing abacavir in whites. Abacavir is a potent HIV-1 nucleoside analogue reverse transcriptase inhibitor which is complicated by a potentially life threatening hypersensitivity syndrome in about 5% of cases. These reactions are characterized by skin rash, gastrointestinal and respiratory manifestations and can occasionally be fatal, particularly on drug rechallenge. Prospective screening for HLA-B*5701 decreased abacavir hypersensitivity reaction incidence in mix French population from 12% before screening to 0% after screening, and the rate of unwarranted interruptions of abacavir therapy decreased from 10.2% to 0.73%. (Zucman et al., J Acquir Immune Defic Syndr 2007)

Human immunodeficiency virus (HIV) infection and acquired immune deficiency syndrome (AIDS) is a significant health problem. By the end of year 2006, 32.2 million individuals were infected and living with HIV worldwide. In 2006 alone, 2.5 million new HIV infection with 2.1 million HIV-related deaths or 5,760 people deaths daily occurs, an estimated 32 million people have died from AIDS since the beginning of the pandemic. Approximately 95% of infected patients living in developing countries especially in Africa, Asian and South America. (UNAID/WHO, 2007)

For Thailand, based on an expert Thais working group estimated 1,109,000 people were infected with HIV, 600,600 anticipated deaths, 508,300 people living with HIV that required continuing care and treatment and 17,000 new cases for 2006 (www.epid.moph.go.th). While the incidence and mortality keeps reducing in Thailand, the delivery of appropriate cares of those who infected prolong patient' life and increase the quality of life.

High Active Antiretroviral Therapy (HAART), the combination of at least three antiretroviral agents comprising at least two NRTIs (Nucleoside Reverse Transcriptase Inhibitors) in combination with at least 1 NNRTI (Non-Nucleoside Reverse Transcriptase Inhibitor) or 1-2 PI (Protease Inhibitor) taken concurrently, represents the current standard of care with antiretroviral therapy. The goal of HAART is to suppress HIV replication to a level below the limit of detection by viral load assays and dramatically improve the patient immune function that results in reduced HIV-related morbidity and mortality and improve quality of life. (aidinfo.nih.gov/ContentFiles/AdultandAldolescentGL.pdf)

Thailand's National Access to Antiretroviral Program for People living with HIV/AIDS (NAPHA) and The Universal health care policy of Thailand were implemented nationwide of antiretroviral therapy to different levels of the public health system increasing dramatically with the number of patients who receiving antiretroviral drug especially GPO-VIR, the fixed-dose combination of stavudine, lamivudine and nevirapine, produced by the Government Pharmaceutical Organization (GPO). GPO-VIR can be taken only 2 tablets per day with the affordably prices making it has been recommended as the first line drug in Thailand.

Non-Nucleoside Reverse Transcriptase Inhibitors comprising nevirapine (NVP), efavirenz (EFV) and dilavirdine (DLV) bind directly to reverse transcriptase enzyme, the binding stops the ability of the reverse transcriptase in replication process. Cutaneous adverse drug reaction is a common side effect of all three NNRTIs. Efavirenz and nevirapine has been recommended as the first line drug in Thailand 2006/2007 because of its effectiveness, easy to administrate with good adherence, excellent food compatibility with affordable prices. Efavirenz has not been made available in combination pill format, patient has to take 7-8 pills per day compare to fixed combination pill consisted of nevirapine as a backbone. EFV is teratogenic and contraindicated in pregnancy, Currently Dilavirdine is not available in majority of developing countries.

EFV is a good alternative for NVP, when hypersensitivity or hepatitis develop in patients who took NVP, The common side effects of EFV included but not limited to drug rash, hepatitis. Both of these side effects had been found less frequent than NVP at rate of 11% and 9% respectively. Central nervous system side effects are more pronounced with EFV, the symptoms include dizziness, vivid dream confusion, suicidal idea, all of these CNS side effects are usually resolved spontaneously after 2 weeks of drug intake (Lee et al., Int Conf AIDS. 2004).

Nevirapine can be used as a single dose intervention peripartum for the prevention of mother-to-child transmission of HIV. It represents an attractive option for patients who must take antiretroviral medications and who prefer a protease inhibitor-sparing regimen as drug resistance regimen. Although antiretroviral therapy is known for its effective treatment, the adverse reaction of drugs is the cause of concern for prescription of NVP. In HIV patients with nevirapine treatment, between 16%-48% of patients reported rash. Second to rash development is hepatitis that can be found in 7-15.6% including fever, nausea, vomiting and dizziness. Furthermore 0.5%-4% of patients eventually developed Stevens-Johnson syndrome (SJS) or Toxic epidermal Necrolysis.

The mechanism of nevirapine-induced skin rash is unknown. Some clinical features or characteristics that were associated with nevirapine-induced skin rash had been described such as female gender, low body weight, pretreatment with antiretroviral drugs prior to the nevirapine treatment, a higher level of the number of CD4-positive cells at the beginning of the treatment and HLA typing (de Maat[n 1] et al., Eur J Clin Pharmacol 2003; Kiertiburanakul et al., Curr HIV Res 2008). The current recommendation for initiation of NVP is for women with CD4<250 cells/mm$^3$ and for men who has CD4<400 cells/mm$^3$ when the indication for HAART fulfilled. (Baylor et al, 2004 and Sanne et al, 2005) In order to reduce the chance of hypersensitivity reaction, it was recommended that treatment should start with 200 mg single dose daily nevirapine for 14 days (lead-in), and followed by 200 mg twice daily. Monitoring of rash and hepatitis is recommended for the first three months.

Human Leukocyte Antigen is part of Major Histocompatibility Complex (MHC) on chromosome 6, the region covers 3.5 million base pairs, the HLA translated into a glycoprotein on the cell surface of immunology related cells and react to intruder antigens. HLA can be classified into three groups 1) Class I antigen (HLA-A, HLA-B and HLA-C). This class is attached to the exogenous antigens or drugs and introduce the foreign antigens to immune cells such as T lymphocyte. T lymphocyte can be stimulated and kill the cell invaded by drugs or foreign organisms. 2) Class II antigens (HLA-DR, HLA-DP and HLA-DQ) are the proteins that attached to endogenous protein and presented those protein to the B lymphocyte to produce antibody to the exogenous antigen. 3) Class III genes is the left over of the class I and class II, function in complement, hormone and intracellular peptide processing.

The hypersensitivity reactions of an antiretroviral drug, abacavir, had been extensively studied and its association to the HLA-B*5701 allele in Caucasians have been strongly implicated with odds ratios 117, negative predictive value more than 90% in every ethnic studies, but highly variable positive predictive value due to variability of HLA-B*5701 allele frequencies in each population. (Mallal et al., Lancet 2002; Hetherington et al., Lancet 2002; Martin et al., Proc Natl Acad Sci 2004).

Association study in hypersensitivity to nevirapine by Martin et al had reported that HLA-DRB1*0101 in patient with high CD4 level may determine susceptibility to nevirapine hepatitis with 40% positive predictive value and 96% negative predictive value (Martin et al., AIDS 2005). However this result had never been confirmed and no single HLA allele were associated with cutaneous adverse reactions from nevirapine in the study.

SUMMARY OF INVENTION

The present invention provides a method of predicting the risk of a patient for developing cutaneous adverse drug reactions induced by NNRTIs. It was discovered that an HLA-B allele, HLA-B*3505 and/or variations on CCHCR1 gene are associated with skin rash that is induced by non nucleoside reverse transcriptase inhibitors such as nevirapine.

Accordingly, the present application provides a method of assessing the risk of a patient for developing a cutaneous adverse drug reaction comprising maculopapular (MP), erythema multiforme (EM), urticaria, angioedema, fixed drug eruption, Steven Johnson's Syndrome (SJS) and Toxic Epidermal Necrosis (TEN) induced by NNRTIs such as nevirapine. The present application provides a method of screening the risk of a patient for developing a cutaneous adverse drug reaction in response to a drug, comprising performing genotyping of an allele HLA-B*3505 or variations on gene CCHCR1 using a biological sample from the patient. Patients with HLA-B*3505 and/or variations on CCHCR1 gene are at risk of development of cutaneous adverse drug reaction from NNRTIs such as nevirapine. Avoidance of nevirapine in these patients is preferable. HLA-B*3505 and/or variations on CCHCR 1 are important for understanding the pathogenesis of cutaneous adverse drug reaction in Thais HIV infected patients. The HLA-B*3505 allele and/or variations on CCHCR1 are supposed to be important in other population where these alleles presented.

Specifically, one aspect of the present invention provides a method of assessing the risk of a patient for the developing a cutaneous adverse drug reaction in response to a drug, comprising determining the presence of HLA-B*3505 alleles by determination of Deoxyribonucleic acid (DNA) or Ribonucleic acid (RNA) or protein or by mean of molecules interacting with HLA-B. The allele and genetic markers can be detected by using any method known in the art. For example, the presence of the allele can be determined by using an oligonucleotide that specifically hybridizes with the nucleic acid coding for the allele. The genetic markers can be selected from the group of genetic marker of the variations consisting of rs1140412, rs4997054, rs9461684, rs3179865 and rs707912, which is the proxy of HLA-B*3505.

The presence of the allele of interest can also be determined by detecting an equivalent genetic marker of the allele, which is a genetic marker that is in linkage disequilibrium to the allele. An equivalent genetic marker can be, e.g., an SNP (single nucleotide polymorphism), microsatellite marker or any genetic polymorphisms. For example, the markers of HLA-B*3505 allele haplotype include, without being limited to, rs1140412, rs4997054, rs9461684, rs3179865 and rs707912. In other words, the presence of the rs1140412, rs4997054, rs9461684, rs3179865 and rs707912.haplotye, rather than the alleles per se, is indicative of a risk for cutaneous adverse drug reactions.

One aspect of the present invention provides a method of assessing the risk of a patient for the developing a cutaneous adverse drug reaction in response to a drug, comprising determining the presence of variation in CCHCR1 gene by determination of Deoxyribonucleic acid (DNA) or Ribonucleic acid (RNA) or protein or by mean of molecules interacting with HLA-B. The allele and genetic markers can be detected by using any method known in the art. For example, the presence of the allele can be determined by using an oligonucleotide that specifically hybridizes with the nucleic acid coding for the allele. The genetic markers can be selected from the group of genetic marker of the variations consisting of rs746647 and rs1265112, of which is indicative of a risk for cutaneous adverse drug reactions.

The presence of the allele of interest can also be determined by detecting an equivalent genetic marker of the allele, which is a genetic marker that is in linkage disequilibrium to the allele. An equivalent genetic marker can be, e.g., an SNP (single nucleotide polymorphism), microsatellite marker or any genetic polymorphisms. For example, the markers of at risk CCHCR1 allele and haplotype include, without being limited to, rs746647 and rs1265112. In other words, the presence of the rs746647 and rs1265112, rather than the alleles per se, is indicative of a risk for cutaneous adverse drug reactions.

One aspect of the present invention provides a method of assessing the risk of a patient for the developing a cutaneous adverse drug reaction in response to a drug, such as nevirapine. The cutaneous adverse drug reaction comprised of maculopapular (MP), erythema multiforme (EM), urticaria, angioedema, fixed drug eruption, Steven Johnson's Syndrome (SJS) and Toxic Epidermal Necrosis (TEN). HLA-B*3505 or variations in CCHCR1 or variations in TCF19 or variations in POLR3G or rs9461681 or rs6545803 is indicative of nevirapine induced cutaneous adverse drug reaction.

Further provided is a method of screening and/or identifying medicines that can be used to treat drug-induced cutaneous adverse drug reactions by determining the presence of HLA-B*allele and/or variation in CCHCR1, TCF19, POLR3G gene as a target in drug development. For example, cells expression any of the alleles or genes can be contacted with medicine candidates, and the candidates that binds to the allele are likely to inhibit the function of the allele. The efficacy of the allele-binding candidate in treating drug induced reactions can then be further tested.

DESCRIPTION OF EMBODIMENTS

Figure 1:
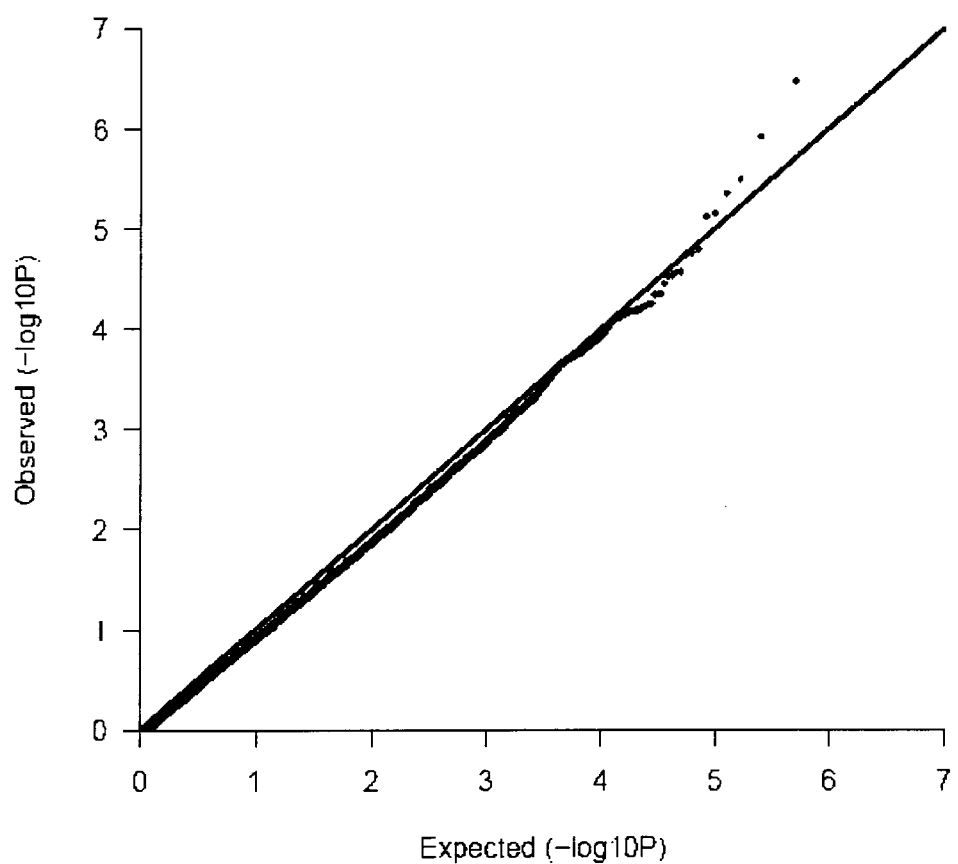
FIG. 1 is The quantile-quantile plot showing the distribution of observed statistics by allelic test for all utilized 499,730 SNPs from genome-wide association study of 72 patients with nevirapine (NVP)-induced skin rash (cases) and 77 tolerant controls. The diagonal line shows the values expected under the null hypothesis.

The present invention provides a method of predicting the risk of a patient for developing cutaneous adverse drug reaction to non-nucleoside antiviral compounds, including nevirapine. It was discovered that HLA-B*3505, polymorphisms in the CCHCR1 gene, TCF19 gene, POLR3G gene, rs9461684 and rs6545803 are associated with cutaneous adverse drug reaction that is induced by nevirapine.
HLA We performed a step-wise case-control association study (EXAMPLE 1) was conducted. The first set of samples consisted of 80 samples from patients with NVP-induced skin rash and 80 samples from NVP-tolerant subjects. These patients were genotyped for the HLA-A, HLA-B, HLA-C, HLA-DRB1, HLA-DPB1 and HLA-DQB1 by a sequence-based HLA typing method. Subsequently, we verified HLA alleles that showed a possible association in the first screening using an additional set of samples consisting of 67 cases with NVP-induced skin rash and 105 controls.

An HLA-B*3505 allele revealed a significant association with NVP-induced skin rash in the first and second screenings. In the combined data set, the HLA-B*3505 allele was observed in 17.5% of the patients with NVP-induced skin rash compared with only 1.1% observed in NVP-tolerant patients (OR=18.96; 95% CI=4.87-73.44, Pc=$4.6 \times 10^{-6}$) and 0.7% in general That population (OR=29.87; 95% CI=5.04-175.86, Pc=$2.6 \times 10^{-5}$). The logistic regression analysis also indicated HLA-B*3505 to be significantly associated with skin rash with OR of 49.15 (95% CI=6.45-374.41, P=0.00017).
CCHCR1

We carried out a genome-wide association (GWA) study (EXAMPLE 2) of 72 individuals with nevirapine (NVP)-induced skin rash and 77 NVP-tolerant controls and further evaluated selected SNPs in a replication sample set (88 cases and 145 controls) in That HIV-infected patients. Of 200 loci followed up, we found significant associations of 2 SNPs (rs1265112 and rs746647) of CCHCR1 with NVP-induced skin rash; a combination of two data set revealed P value of $1.2 \times 10^{-8}$ (GWA, $2.7 \times 10^{-4}$; replication, $1.2 \times 10^{-5}$). Finally, 15 SNPs around CCHCR1 revealed significant associations with susceptibility to NVP-induced skin rash in That HIV patients.

EXAMPLES

Example 1

HLA-B*3505

Study Population

A case-control study was conducted using HIV-infected That patients who visited (i) Infectious Disease Clinic, Ramathibodi Hospital, Mahidol University, (ii) Bamrasnaradura Infectious Disease Institute, Ministry of Public Health, or (iii) Department of Preventive Medicine, Faculty of Medicine, Srinakharinwirot University, Thailand. The enrollment of 80 skin-rash cases and 80 NPV-tolerant patients for the first set of samples was done between March and December, 2006. To verify a possible association in the initial screening, the second set of samples consisting of 67 skin-rash patients and 105 controls was enrolled between January and June, 2007.

Inclusion criteria were adult HIV-infected patients (>15 years old) who were treated with GPO-VIR®. Each eligible patient was followed up for at least 6 months after the initiation of NVP treatment or until they developed skin rash. Patients were categorized into case and control groups according to a presence or an absence of skin rash. The control group was defined as the patient who had been treated with NVP for at least 6 months and developed no sign of cADRs. The case group was defined to be those having the skin rash within 6 months after the beginning of NVP treatment. The diagnosis of the NVP-induced rash was reviewed and given by infectious disease specialists. Severity of rash was categorized according to Division of AIDS table for grading the severity of adult and pediatric adverse events, National Institute of Allergy and Infectious Disease (NIAID)/National Institutes of Health (NIH). Briefly, grade 1: a localized macular rash; grade 2: diffuse macular, maculopapular, or morbilliform rash or target lesions; grade 3: diffuse macular, maculopapular, or morbilliform rashes with vesicles or a limited number of bullae or superficial ulcerations of mucous membrane limited to one site; and grade 4: extensive or generalized bullous lesions, SJS, ulceration of mucous membrane involving more than two distinct mucosal sites, or TEN. Collection of blood samples and clinicopathological information were undertaken with informed consent and approved by the Institutional Review Boards. This study was conducted in accordance with the principles of the Declaration of Helsinki.
DNA Isolation Genomic DNA was isolated with a standard phenol-chloroform extraction protocol and re-suspended in Tris-HCl buffer (pH 8.5). Their concentration was quantified using a UV spectrophotometer ND-1000 (NanoDrop Technologies, Wilmington, Del.). The purity was determined by calculating the ratio of absorbance at 260-280 nm.
HLA Genotyping Genotypes in HLA-A, HLA-B, HLA-C, HLA-DRB1, HLA-DPB1 and HLA-DQB were determined by sequence-based typing (SBT) using the AlleleSEQR Sequenced Based Typing Kits (Atria Genetics, South San Francisco, Calif.), according to the manufacturer's instructions. Briefly, the primary amplification reaction consists of PCR pre-mix reagent, AmpliTaq Gold and 20 ng/μl genomic DNA. The PCR products were purified using ExoSAP-IT and sequenced in the forward and reverse orientations. Finally, the reaction products were reconstituted with 15 μl of Hi-Di™ formamide (Applied Biosystems, Foster City, Calif.), ran on the ABI 3730xl DNA Analyzer (Applied Biosystems) and genotype calling were made by Assign SBT™ 3.2.7 software (Conexio Genomics, Perth, Australia). HLA alleles showing a possible association (Pc-value <0.05) with NPV-induced skin rash in the first screening were verified in the second set of samples. Allelic frequency of HLA regions in the general That population was obtained from the published information.

Statistical Analysis

Dichotomous variables between the two groups were compared by Fisher's exact tests. Continuous variables were compared by the Mann-Whitney U test. Odds ratios were calculated with Haldane's modification, which add 0.5 to all cells to accommodate possible zero counts [28]. All P-values were two-tailed, P<0.05 was considered to indicate possible statistical significance. The corrected P (Pc) values were adjusted by applying Bonferroni's correction for 93 tests (14 for HLA-A, 20 for HLA-B, 16 for HLA-C, 18 for HLA-DRB1, 12 for HLA-DQB1 and 13 for HLA-DPB1).

A multivariate logistic regression model was constructed including clinical variables that had been shown to be associated with NVP-induced skin rash and HLA-B*3505 status of the patients was constructed. HLA-B*3505 was coded according to the presence of HLA-B*3505 under a dominant model. In accordance with previous study (Kiertiburanakul et al., Curr HIV Res 2008), the CD4 cell count just before the initiation of the NVP treatment was grouped into intervals of 50 cells/mm$^3$. The clinical information including the history of drug allergy and AIDS defining illness were also included in the model. The additive assumption was assessed by introducing possible clinical variables which interact with HLA-B*3505 status into the model. The interaction terms with the P-value of more than 0.05 were considered to be not significant, and then the factors were excluded from the final model. All statistic analyses were performed using the R statistic program.

Characteristics of Patients and Controls

Demographic variables, immunological status, available liver function tests, history of drug allergy, concurrent medications, time from the first exposure to develop skin rash and their severity of 147 patients with NVP-induced skin rash (80 and 67 cases from the first and second recruitments, respectively) and 185 controls (80 and 105 subjects from the first and second recruitments, respectively) are summarized in Tables 1 and 2. The median time to develop rash was 12 days (interquartile range (IQR), 8-22). Among the 147 NPV-induced rash cases, 13 patients (9%) were classified as grade 1, 51 (35.7%) as grade 2, 68 (47.6%) as grade 3 and 11 (7.7%) as grade 4. The distribution of gender, age, body weight, history of AIDS defining-illness and liver function tests at the initiation of NVP treatment in the case group showed no difference to those in the tolerant control. However, the proportion of the patient with history of drug allergy, concurrent medications as well as the number of CD4-positive cells at the beginning of the NVP treatment were higher in the case group than the control group (P<0.001, P=0.003 and P=0.005, respectively). Whereas the proportion of the patients with prescribed lead-in of NVP was higher in the control than in the case group.

Association Between HLA-B*3505 and NVP-Induced Skin Rash

By DNA sequencing, we determined genotypes at the HLA-A, HLA-B, HLA-C, HLA-DRB1, HLA-DQB1 and HLA-DPB1 loci in the first set of case and control groups. The results of the first screening are summarized in Table 3; HLA-A*2407, HLA-B*3505, HLA-Cw*0401, and HLA-DRB1*1202 alleles were observed at the significantly higher frequencies in the case group than the control group. On the other hand, HLA-B*3802 and HLA-Cw*0702 were found to be significantly lower in the case group than the control group. After the stringent Bonferroni's correction, only HLA-B*3505 remained significantly different between case and control groups (Pc=3.5×10$^{-2}$). The HLA-B*3505 was present in 9.9% of the patients with NVP-induced skin rash, but only 0.7% in the NVP-tolerant group. Guided by the patients who were HLA-B*3505 carriers, we analyzed the allelic distribution of the combined HLA loci and defined the extended haplotype. The most common haplotype combination, HLA-Cw*0401-HLA-B*3505 was present in 7.8% of the patients with NVP-induced skin rash, but only 0.7% in the tolerant group. While the statistical evidence from the haplotype analysis is not directly comparable with the univariate analysis, the higher effect size of HLA-B*3505 and robust statistical evidence after Bonferroni's correction supported this allele(s) or those in linkage disequilibrium with this allele as the causative genetic variation.

We further genotyped HLA-B locus to confirm the association of HLA-B*3505 in 67 NVP-induced skin rash patients and 105 tolerant controls. The results are summarized in Table 4. In concordance with the first screening, HLA-B*3505 also showed an association with NVP-induced skin rash when comparing individual carrying HLA-B*3505 among the case and control groups in the second screening (Pc=1.4×10$^{-2}$). When the combined data set was analyzed, the HLA-B*3505 allele was presented in 17.5% (25 of 143 subjects) in patients with NVP-induced skin rash, but only 1.1% (2 of 181 subjects) in NVP-tolerant group (OR=18.96; 95% CI=4.87-73.44; Pc=4.6×10$^{-6}$), and only 0.7% (1 of 142 subjects) in the general That population (OR=29.87; 95% CI=5.04-175.86; Pc=2.6×10$^{-5}$).

We further analyzed an association of HLA-B*3505 according to the severity of skin rash. Patients with grade 1 and 2 severities were grouped together into a "mild to moderate rash" group and those with grade 3 and 4 into a "severe rash" group (Table 4). The result revealed significantly higher frequencies of HLA-B*3505 in both groups than the NVP-tolerant group (Pc=6.8×10$^{-4}$ and Pc=1.2×10$^{-4}$, respectively). Thus, the association of HLA-B*3505 with the NVP-induced skin rash is likely to be independent on the severity, indicating that HLA-B*3505 may be important for the initiation of the immune response to cause skin rash.

Logistic Regression Analysis

Since subsequent multiple logistic regression analysis including the information of concomitant drugs indicated that this variable was not associated with cADRs after adjusting for other variables, we had excluded this variable from the final logistic model. The variables included in the final logistic regression model, the odds ratios and their significant levels are presented in Table 5. The HLA-B*3505 status (OR=49.15; 95% CI=6.45-374.41; P=0.00017), positive history of drug allergy (OR=2.83; 95% CI=1.47-5.45; P=0.0019), and the number of CD4 cells prior to the NVP treatment (OR=1.11 for each 50 cells/mm$^3$ increment; 95% CI=1.03-1.20; P=0.0076) were found to be significantly associated with the risk of skin rash. While the regimen of the lead-in dosing of NVP significantly decreased the risk of skin rash (OR=0.48; 95% CI=0.28-0.82; P=0.0073). The interactions between the HLA-B*3505 and other variables were not statistically significant when included in the multivariate logistic regression (data not shown).

5 SNPs for the Prediction of HLA-B*3505

By reading HLA-B sequences from all subjects, we can identified 5 SNPs including rs9461684 (allele A), rs707912 (allele T), rs4997052 (allele C), rs3179865 (allele C) and rs1140412 (allele C) for the prediction of HLA-B*3505 carriers in That population (Table 6).

TABLE 1

Clinical, immunological and demographical characteristics of the patients exposed to antiretroviral therapy with or without nevirapine (NVP)-induced cutaneous adverse drug reactions

| Characteristic | First screening | | | Second screening | | |
|---|---|---|---|---|---|---|
| | NVP-rash (n = 80) | NVP-tolerant (n = 80) | P value | NVP-rash (n = 67) | NVP-tolerant (n = 105) | P value |
| Gender, n (%) | | | 1.00 | | | 0.041 |
| Male | 38 (47.5) | 37 (46.3) | | 25 (37.3) | 57 (54.3) | |
| Female | 42 (52.5) | 43 (53.8) | | 42 (62.7) | 48 (45.7) | |
| Age (years), median (IQR) | 35.7 (31.4-41.1) | 35.1 (30.8-41.9) | 0.61 | 37 (32.5-42.8) | 35.5 (31.9-41.6) | 0.40 |
| Body weight (kg), median (IQR) | 54 (48.5-60.5) | 54.5 (48-64) | 0.68 | 52 (46-58.7) | 55 (50-63) | 0.039 |
| AIDS defining-illness, n (%) | 34 (42.5) | 44 (55) | 0.15 | 45 (67.2) | 59 (56.2) | 0.20 |
| Prescribed lead-in, n (%) | 47 (58.8) | 60 (75) | 0.043 | 33 (50.8) | 78 (77.2) | 0.00066 |
| CD4 cell value at NVP initiation, median (IQR) | | | | | | |
| CD4 cell count (cells/mm$^3$) | 206 (77-367) (n = 80) | 63 (21-203) (n = 78) | 0.00010 | 76.5 (33.5-178.5) (n = 64) | 69 (20.3-211) (n = 103) | 0.60 |
| CD4 percentage | 12 (5-17) (n = 80) | 6.5 (2-11.5) (n = 80) | 0.00070 | 6 (3-10.3) (n = 62) | 6 (2-11) (n = 98) | 0.92 |
| Liver function test at NVP initiation, median (IQR) | | | | | | |
| AST (mg/dL) | 31 (22.5-49.5) (n = 36) | 27.5 (21-43) (n = 42) | 0.30 | 30 (22.3-39) (n = 39) | 28 (23-44.8) (n = 55) | 0.81 |
| ALT (mg/dL) | 49 (36.3-78.8) (n = 39) | 40.5 (30-58) (n = 46) | 0.071 | 39.5 (22-53) (n = 39) | 42 (32-52) (n = 58) | 0.31 |

| Characteristic | Total | | |
|---|---|---|---|
| | NVP-rash (n = 147) | NVP-tolerant (n = 185) | P value |
| Gender, n (%) | | | 0.15 |
| Male | 63 (42.9) | 94 (50.8) | |
| Female | 84 (57.1) | 91 (49.2) | |
| Age (years), median (IQR) | 36.4 (32.1-42.5) | 35.5 (31.6-41.8) | 0.46 |
| Body weight (kg), median (IQR) | 53 (47-60) | 55 (49-64) | 0.094 |
| AIDS defining-illness, n (%) | 79 (53.7) | 103 (55.7) | 0.74 |
| Prescribed lead-in, n (%) | 80 (55.2) | 138 (76.2) | 0.000085 |
| CD4 cell value at NVP initiation, median (IQR) | | | |
| CD4 cell count (cells/mm$^3$) | 154.5 (45.5-249) (n = 144) | 69 (20.8-209) (n = 181) | 0.00040 |
| CD4 percentage | 8 (4-14) (n = 142) | 6 (2-11) (n = 178) | 0.0048 |
| Liver function test at NVP initiation, median (IQR) | | | |
| AST (mg/dL) | 30 (22.3-42.8) (n = 75) | 28 (21.8-44) (n = 97) | 0.61 |
| ALT (mg/dL) | 43 (31-64) (n = 81) | 42 (30.5-56.5) (n = 104) | 0.53 |

P values were calculated by Fisher's exact test (dichotomous variables) and the Mann-Whitney U test (continuous variables) comparing between NVP-induced skin rash patients with those of the NVP-tolerant controls. AST, aspartate aminotransferase; ALT, alanine aminotransferase; IQR, interquartile range.

TABLE 2

Clinical, immunological and demographical characteristics of the patients exposed to antiretroviral therapy with or without nevirapine (NVP)-induced cutaneous adverse drug reactions (continued)

| Characteristic | First screening | | | Second screening | | | Total | | |
|---|---|---|---|---|---|---|---|---|---|
| | NVP-rash (n = 80) | NVP-tolerant (n = 80) | P value | NVP-rash (n = 67) | NVP-tolerant (n = 105) | P value | NVP-rash (n = 147) | NVP-tolerant (n = 185) | P value |
| History of drug allergy [a], n (%) | 16 (20) | 10 (12.5) | 0.28 | 20 (29.9) | 9 (8.6) | 0.00061 | 36 (24.5) | 19 (10.3) | 0.00061 |
| Sulfamethozaxole | 14 (17.5) | 5 (6.3) | 0.048 | 13 (19.4) | 5 (4.8) | 0.0039 | 27 (18.4) | 10 (5.4) | 0.00033 |
| Dapsone | 3 (3.8) | 0 (0) | 0.25 | 3 (4.5) | 1 (1) | 0.30 | 6 (4.1) | 1 (0.5) | 0.047 |
| Penicillin | 1 (1.3) | 0 (0) | 1.00 | 1 (1.5) | 0 (0) | 0.39 | 2 (1.4) | 0 (0) | 0.20 |
| Carbamazepine | 0 (0) | 0 (0) | 1.00 | 1 (1.5) | 0 (0) | 0.39 | 1 (0.7) | 0 (0) | 0.44 |
| Anti-tuberculous drugs | 0 (0) | 2 (2.5) | 0.50 | 0 (0) | 3 (2.9) | 0.28 | 0 (0) | 5 (2.7) | 0.069 |
| Others | 6 (7.5) | 4 (5) | 0.75 | 6 (9) | 2 (1.9) | 0.057 | 12 (8.2) | 6 (3.2) | 0.055 |
| Concomitant drugs [b], n (%) | 34 (42.5) | 55 (68.8) | 0.0014 | 44 (67.7) | 74 (71.2) | 0.73 | 78 (53.8) | 129 (70.1) | 0.0028 |
| Fluconazole | 15 (18.8) | 33 (41.3) | 0.0031 | 26 (42.6) | 42 (40.4) | 0.87 | 41 (29.1) | 75 (40.8) | 0.035 |
| Co-trimoxazole | 15 (18.8) | 18 (22.5) | 0.70 | 29 (43.3) | 36 (34.6) | 0.26 | 44 (29.9) | 54 (29.3) | 1.00 |
| Dapsone | 1 (1.3) | 2 (2.5) | 1.00 | 8 (11.9) | 5 (4.8) | 0.14 | 9 (6.1) | 7 (3.8) | 0.44 |
| Anti-tuberculous drugs | 5 (6.3) | 4 (5) | 1.00 | 5 (7.5) | 12 (11.5) | 0.44 | 10 (6.8) | 16 (8.7) | 0.55 |

TABLE 2-continued

Clinical, immunological and demographical characteristics of the patients exposed to antiretroviral therapy with or without nevirapine (NVP)-induced cutaneous adverse drug reactions (continued)

|  | First screening | | | Second screening | | | Total | | |
|---|---|---|---|---|---|---|---|---|---|
| Characteristic | NVP-rash (n = 80) | NVP-tolerant (n = 80) | P value | NVP-rash (n = 67) | NVP-tolerant (n = 105) | P value | NVP-rash (n = 147) | NVP-tolerant (n = 185) | P value |
| Others | 3 (3.8) | 2 (2.5) | 1.00 | 2 (3) | 6 (5.8) | 0.48 | 5 (3.4) | 8 (4.3) | 0.78 |
| Time to develop rash (days), median (IQR) | 12 (7-22) | Not observed | | 14 (10-21) | Not observed | | 12 (8-22) | Not observed | |
| Severity of rash, n (%) | | | | | | | | | |
| Grade 1 | 0 (0) | Not observed | | 13 (20.3) | Not observed | | 13 (9) | Not observed | |
| Grade 2 | 28 (35.4) | Not observed | | 23 (36) | Not observed | | 51 (35.7) | Not observed | |
| Grade 3 | 50 (63.3) | Not observed | | 18 (28.1) | Not observed | | 68 (47.6) | Not observed | |
| Grade 4 | 1 (1.3) | Not observed | | 10 (15.6) | Not observed | | 11 (7.7) | Not observed | |

[a] Some patients had more than one drug to cause allergy.
[b] Some patients took more than one concomitant drug.
P values were calculated by Fisher's exact test (dichotomous variables) and the Mann-Whitney U test (continuous variables) comparing between NVP-induced skin rash patients with those of the NVP-tolerant controls. IQR, interquartile range.

TABLE 3

First screening association of HLA alleles and haplotypes with nevirapine (NVP)-induced cutaneous adverse drug reactions

|  | All examined alleles | | n (%) | | | | |
|---|---|---|---|---|---|---|---|
| MHC marker | NVP-rash | NVP-tolerant | NVP-rash | NVP-tolerant | P value | Pc value | Odds ratio (95% CI) |
| HLA-A | | | | | | | |
| *2407 | 128 | 144 | 10 (7.8) | 1 (0.7) | $3.6 \times 10^{-3}$ | NS | 12.12 (1.96-74.24) |
| HLA-B | | | | | | | |
| *3505 | 152 | 152 | 15 (9.9) | 1 (0.7) | $3.8 \times 10^{-4}$ | $3.5 \times 10^{-2}$ | 16.53 (2.74-98.98) |
| *3802 | 152 | 152 | 3 (2) | 13 (8.6) | $1.8 \times 10^{-2}$ | NS | 0.22 (0.07-0.72) |
| HLA-Cw | | | | | | | |
| *0401 | 128 | 144 | 17 (13.3) | 4 (2.8) | $1.3 \times 10^{-3}$ | NS | 5.36 (1.83-15.60) |
| *0702 | 128 | 144 | 14 (10.9) | 34 (23.6) | $6.7 \times 10^{-3}$ | NS | 0.40 (0.20-0.78) |
| HLA-DRB1 | | | | | | | |
| *1202 | 160 | 160 | 41 (25.6) | 19 (11.9) | $2.4 \times 10^{-3}$ | NS | 2.56 (1.41-4.61) |
| Haplotype | | | | | | | |
| A*2407, B*3505 | 128 | 144 | 6 (4.7) | 1 (0.7) | NS | NS | 7.03 (1.09-44.94) |
| Cw*0401, B*3505 | 128 | 144 | 10 (7.8) | 1 (0.7) | $3.6 \times 10^{-3}$ | NS | 12.12 (1.96-74.24) |
| B*3505, DRB1*1202 | 128 | 144 | 6 (4.7) | 1 (0.7) | NS | NS | 7.03 (1.09-44.94) |
| A*2407, Cw*0401, B*3505 | 128 | 144 | 6 (4.7) | 1 (0.7) | NS | NS | 7.03 (1.09-44.94) |
| A*2407, B*3505, DRB1*1202 | 128 | 144 | 5 (3.9) | 1 (0.7) | NS | NS | 5.81 (0.88-37.92) |
| Cw*0401, B*3505, DRB1*1202 | 128 | 144 | 6 (4.7) | 1 (0.7) | NS | NS | 7.03 (1.09-44.94) |
| A*2407, Cw*0401, B*3505, DRB1*1202 | 128 | 144 | 5 (3.9) | 1 (0.7) | NS | NS | 5.81 (0.88-37.92) |

P values were calculated by Fisher's exact test comparing the positive alleles of NVP-induced skin rash patients with those of the NVP-tolerant controls and of the general population controls. Pc values were adjusted by using Bonferroni's correction for multiple comparisons (14 for HLA-A, 20 for HLA-B, 16 for HLA-C, 18 for HLA-DRB1, 12 for HLA-DQB1 and 13 for HLA-DPB1). CI, confidence interval; n, number of positive allele; NS not significant (P > 0.05); Pc value, corrected P value.

TABLE 4

Risk HLA allele of nevirapine (NVP)-induced cutaneous adverse drug reactions, HLA-B*3505

|  | All subjects | | n (%) | | | | |
|---|---|---|---|---|---|---|---|
| Screening | NVP-rash | NVP-tolerant | NVP-rash | NVP-tolerant | P value | Pc value | Odds ratio (95% CI) |
| First | 76 | 76 | 14 (18.4) | 1 (1.3) | $5.5 \times 10^{-4}$ | $5.1 \times 10^{-2}$ | 16.94 (2.75-102.82) |
| Second | 67 | 105 | 11 (16.4) | 1 (1) | $1.5 \times 10^{-4}$ | $1.4 \times 10^{-2}$ | 20.43 (3.28-125.46) |
| Total | 143 | 181 | 25 (17.5) | 2 (1.1) | $4.9 \times 10^{-8}$ | $4.6 \times 10^{-6}$ | 18.96 (4.87-73.44) |

TABLE 4-continued

Risk HLA allele of nevirapine (NVP)-induced cutaneous adverse drug reactions, HLA-B*3505

| Severity of skin rash | | | | | | | |
|---|---|---|---|---|---|---|---|
| Mild to moderate | 62 | 181 | 11 (17.7) | 2 (1.1) | $7.3 \times 10^{-6}$ | $6.8 \times 10^{-4}$ | 19.30 (4.62-79.84) |
| Severe | 77 | 181 | 14 (18.2) | 2 (1.1) | $1.3 \times 10^{-6}$ | $1.2 \times 10^{-4}$ | 19.89 (4.88-80.30) |

| | Screening | n (%) General population (n = 142)[a] | P value | Pc value | Odds ratio (95% CI) |
|---|---|---|---|---|---|
| | First | 1 (0.7) | $1.8 \times 10^{-6}$ | $1.7 \times 10^{-4}$ | 31.84 (5.20-192.46) |
| | Second | 1 (0.7) | $1.8 \times 10^{-5}$ | $1.7 \times 10^{-3}$ | 27.70 (4.45-169.80) |
| | Total | 1 (0.7) | $2.8 \times 10^{-7}$ | $2.6 \times 10^{-5}$ | 29.87 (5.04-175.86) |
| Severity of skin rash | | | | | |
| | Mild to moderate | 1 (0.7) | $9.5 \times 10^{-6}$ | $8.9 \times 10^{-4}$ | 30.41 (4.88-186.67) |
| | Severe | 1 (0.7) | $2.1 \times 10^{-6}$ | $1.9 \times 10^{-4}$ | 31.33 (5.12-189.38) |

[a]Allelic frequency of HLA regions in the general Thai population was obtained from the published information (www.allelefrequencies).
P values were calculated by Fisher's exact test comparing the positive alleles of NVP-induced skin rash patients with those of the NVP-tolerant controls and of the general population controls. Pc values were adjusted by using Bonferroni's correction for multiple comparisons (14 for HLA-A, 20 for HLA-B, 16 for HLA-C, 18 for HLA-DRB1, 12 for HLA-DQB1 and 13 for HLA-DPB1). CI, confidence interval; n, number of subjects; NS not significant (P > 0.05); Pc value, corrected P value.

TABLE 5

Risk factors for rash by logistic regression

| Factors | Odds ratio (95% Confidence interval) | P value |
|---|---|---|
| HLA-B*3505 | 49.15 (6.45-374.41) | 0.00017 |
| History of drug allergy | 2.83 (1.47-5.45) | 0.0019 |
| Prescribed lead-in | 0.48 (0.28-0.82) | 0.0073 |
| CD4 cell count at NVP initiation, each 50 cells/mm³ increment | 1.11 (1.03-1.20) | 0.0076 |

TABLE 6

Five SNPs prediction of HLA-B*3505 carriers in Thai population

| No. | rs# | Chr pos | Gene | Risk allele | Locus type |
|---|---|---|---|---|---|
| 1 | rs9461684 | 31361413 | 70 kb 3' near HLA-B | A | Biallelic |
| 2 | rs707912 | 31432014 | HLA-B: exon3 | T | Biallelic |
| 3 | rs4997052 | 31432122 | HLA-B: exon3 | C | Triallelic |
| 4 | rs3179865 | 31432172 | HLA-B: exon3 | C | Triallelic |
| 5 | rs1140412 | 31432178 | HLA-B: exon3 | C | Triallelic |

Although the HLA-B*3505 was observed in the significantly higher proportion among the NVP-induced skin rash than the tolerant controls, the frequency was still as low as 17.5% in the case group. However, its specificity is extremely high as 98.9%. Hence, HLA-B*3505 is likely to be one of critical determinants of NVP-induced skin rash and there are additional yet-unidentified genetic and non-genetic factors involved in NVP-induced skin rash. These factors may include the factors reported previously, such as female gender, pretreated with antiretroviral drugs prior to the NVP treatment, the number of CD4-positive cells, and lower levels of HIV RNA. Association of a higher level of the number of CD4-positive cells as a risk factor for NVP-associated rash was also found to be significant in our present study although others were not. In addition to these two factors, the presence of drug allergy history was indicated some relation to development of skin rash in the multivariate logistic regression. Although only 20% of the patients with NVP-induced skin rash had HLA-B*3505, NVP-treated patients who had HLA-B*3505 revealed a very high incidence (25 of 27 patients, 93%) of the skin rash, indicating that HLA-B*3505 can be a very good predictor for a risk of NVP-induced ADRs for That HIV-infected patients.

Strong indication of the possible involvement of the HLA-B*3505 genotype in development of the NPV-induced skin rash provides a novel insight to understanding of the pathogenesis of drug-induced rash in That HIV-infected population. Because of its high specificity in identifying NVP-induced rash, it is possible to utilize the HLA-B*3505 as a marker to avoid NVP-induced rash.

Example 2

CCHCR1

Study Population

A step-wise case-control study was conducted using HIV-infected That patients who visited (i) Infectious Disease Clinic, Ramathibodi Hospital, Mahidol University, (ii) Bamrasnaradura Infectious Disease Institute, Ministry of Public Health, and (iii) Department of Preventive Medicine, Faculty of Medicine, Srinakharinwirot University, Thailand.

Inclusion criteria were adult HIV-infected patients (>15 years old) who were treated with GPO-VIR® Patients were categorized into case and control groups according to a presence or an absence of skin rash. The control group was defined to be patients who revealed no evidence of cutaneous adverse reactions by the NVP therapy for more than 6 months. The case group was defined to be those with the skin rash after NVP exposure. The diagnosis of the NVP-induced rash was reviewed and given by infectious disease specialists. Severity of rash was categorized according to Division of AIDS tables for grading the severity of adverse events, National Institute of Allergy and Infectious Disease (NIAID)/National Institutes of Health (NIH). Briefly, grade 1: a localized macular rash; grade 2: diffuse macular, maculopapular, or morbilliform rash or target lesions; grade 3: diffuse macular, maculopapular, or morbilliform rashes with vesicles or a limited number of bullae or superficial ulcerations of mucous membrane limited to one site; and grade 4: extensive or generalized bullous lesions, SJS, ulceration of mucous membrane involving more than two distinct mucosal sites, or TEN. Collection of blood samples and clinicopathological information were undertaken with informed consent and approved by the Institutional Review Boards. This study was conducted in accordance with the principles of the Declaration of Helsinki.

Panel A: The enrollment of NVP-induced skin rash cases and NPV-tolerant patients for the first set of samples has been done between March and December, 2006. Our 72 cases (36 male and 36 female) and 77 controls (36 males and 41 females) were used in the genome-wide association (GWA) study.

Panel B: To verify the possible association in the Panel A, the second set of samples was enrolled between January and June, 2007. Subjects for the replication study consisted of 88 cases (33 males and 55 females) and 145 controls (80 males and 65 females).

DNA Isolation

Genomic DNA was isolated with a standard phenol-chloroform extraction protocol and re-suspended in Tris-HCl buffer (pH 8.5). Their concentration was quantified using a UV spectrophotometer ND-1000 (NanoDrop Technologies, Wilmington, Del.). The purity was determined by calculating the ratio of absorbance at 260-280 nm.

GWA Genotyping

GWA study was conducted in 72 samples from NVP-induced skin rash patients and 77 samples from tolerant controls using Illumina HumanHap550v3 Genotyping BeadChip (San Diego, Calif.), containing more than 500,000 haplotype tagging SNPs derived from phase I of the International HapMap project. The overall call rates of all subjects were more than or equal to 0.98. All cluster plots were checked by visual inspection by trained staff and SNPs with ambiguous calls were excluded. Of all 554,496 SNPs with successful genotyping, 54,756 SNPs were undetermined and additional 10 SNPs showed a significant distortion from Hardy-Weinberg equilibrium in controls ($P<1.0\times10^{-6}$). In total, 54,766 unique SNPs were removed from the study. Finally, 499,730 SNPs on autosomal chromosomes passed the quality control filters and were further analyzed.

Replicated Genotyping

We further evaluated top 200 SNPs showing the smaller P values from the initial GWA study in an independent set of samples consisting 88 skin-rash patients and 145 controls by multiplex PCR-based Invader assay (Third Wave Technologies) or direct sequencing of the PCR products by using 96-capillary 3730xl DNA Analyzer (Applied Biosystems, Foster City, Calif.).

Validated Genotyping

To validate genotyping results of the Illumina HumanHap550v3 Genotyping BeadChip (San Diego, Calif.), we re-genotyped all subjects for Panel A with those top 200 SNPs showing the smaller P values in the initial GWA study by multiplex-PCR based Invader assay or direct sequencing of the PCR products by using 96-capillary 3730xl DNA Analyzer (Applied Biosystems), and SNPs with concordance rates of <98% between two assays (Illumina and Invader assay/direct sequencing) were excluded from the further analysis.

Fine Mapping of CCHCR1

We have done genotyping of all 20 tagging SNPs within the linkage disequilibrium (LD) spanning 30 kb (Chr6: 31214000 . . . 31243800), covering the CCHCR1, TCF19 and some parts of PSOR1C1 and POU5F1, based on the Han Chinese (HCB) HapMap data with $r^2>0.8$ (Table 2) by multiplex-PCR based Invader assay.

Re-Sequencing of CCHCR1

To detect sequence variations of CCHCR1 locus, we screened genomic sequence of this gene, covering exon-intron and untranslated regions. Using the genomic sequence information (GenBank accession number, NC_000006.10 (Chr6: 31217245 . . . 31235424)), we amplify the genomic region from 2 kb upstream of the first exon to 1 kb downstream of the last exon of CCHCR1. The initial screening has been done in the Panel A. For each of the DNA samples for Panel A, PCR was performed with 10 ng of genomic DNA. All PCRs were performed by using GeneAmp PCR system 9700 (Applied Biosystems) and used Ex Taq DNA polymerase (Takara, Tokyo, Japan). We performed PCR with an initial denaturation step of 94° C. for 5 min, followed by 37 cycles of denaturation at 94° C. for 30 s, annealing at 60° C. for 30 s, and extension at 72° C. for 1 min. These cycling reactions were followed by a final extension at 72° C. for 5 min. We carried out SNP discovery by direct sequencing of the PCR products by using 96-capillary 3730xl DNA Analyzer (Applied Biosystems). We sequenced all amplified fragments by two pairs of sequencing primers. All SNPs were detected by the Polyphred computer program (droog.gs.washington.edu/Polyphred.html) and were confirmed by sequencing both strands of each PCR product. The SNPs which found to be significantly associated with NVP-induced skin rash in this panel (P<0.05), were further evaluated in the replication set (Panel B) by multiplex-PCR based Invader assay.

Statistical Analysis

Of all SNPs in this study, Fisher's exact test was applied to two-by-two contingency table in three genetic models: allele 1 versus allele 2, genotype 11 versus 12+22 and genotype 22 versus 11+12. We used GenABEL package in R statistic program to estimate the genetic inflation factor lambda from all utilized 499,730 SNPs that passed the QC filters. Significance level after conservative Bonferroni correction for multiple testing was $P=1.0\times10^{-7}$ (0.05/499,730). Odds ratios and confidence intervals were calculated using the risk genotype(s) as a reference. Statistic analyses were performed using the R statistical environment version 2.7.1 (www.R-project.org). To draw LD map, we used Haploview software.

Results

By using Illumina HumanHap550 BeadChips, we tested 499,730 SNPs for association with NVP-induced skin rash in 72 individuals with rash and 77 tolerant controls in That HIV-infected patients (Panel A). The call rates greater than or equal to 98% were achieved for each. After genotyping all subjects, undetermined SNPs were eliminated from the further analysis. The quantile-quantile plot (FIG. 1) showed no evidence of systematic bias of observed statistics versus expected statistics. The genetic inflation factor (k=1.019) derived from the GWA study, implied that population stratification have been kept at minimal in this sample set.

Subsequently, to verify the findings obtained by the initial GWA study, we further evaluated top 200 SNPs showing the smallest P values (FIG. 2) from the initial GWA analysis in a replication sample set comprising of 88 NVP-rash cases and 145 tolerant controls (Panel B) by multiplex PCR-based Invader assay or direct sequencing. We simultaneously validated genotyping results from the Illumina assay by genotyping all of subjects for Panel A with those top 200 SNPs and comparison of genotyping calls between two assays (Illumina and Invader assay/direct sequencing). SNPs with concordance rates of less than 98% were excluded from the further analysis. The GWA and replication analysis of top 200 SNPs identified several candidate SNPs that might be associated with the disease (Table 7). Analysis of these selected SNPs reveals 5 SNPs on chromosome 6 to be significantly associated with NVP-induced skin rash (P<0.05) in the replication study and these association signals increased in the combined data set. Four of these SNPs locates within an interval of high linkage disequilibrium (LD), spanning 30 kb (Chr6: 31214000 . . . 31243800), covering the CCHCR1, TCF19 and some parts of PSOR1C1 and POU5F1 (FIG. 3). We found strong significant associations of 2 SNPs (rs1265112 and rs746647) in the CCHCR1 locus on chromosome 6p21.3 (Table 7). The combined P value of the two studies was $1.2 \times 10^{-8}$, which remained statistically significant after adjustment for multiple testing, using a conservative Bonferroni's correction for the 499,730 tests. There was 35.63% (57/160) of the patients with NVP-induced skin rash carried the risk allele, but only 11.26% (25/222) in tolerant controls. The odds ratio of the combined data was 4.36 (95% confidence interval (CI): 2.58-7.36).

Figure 4:
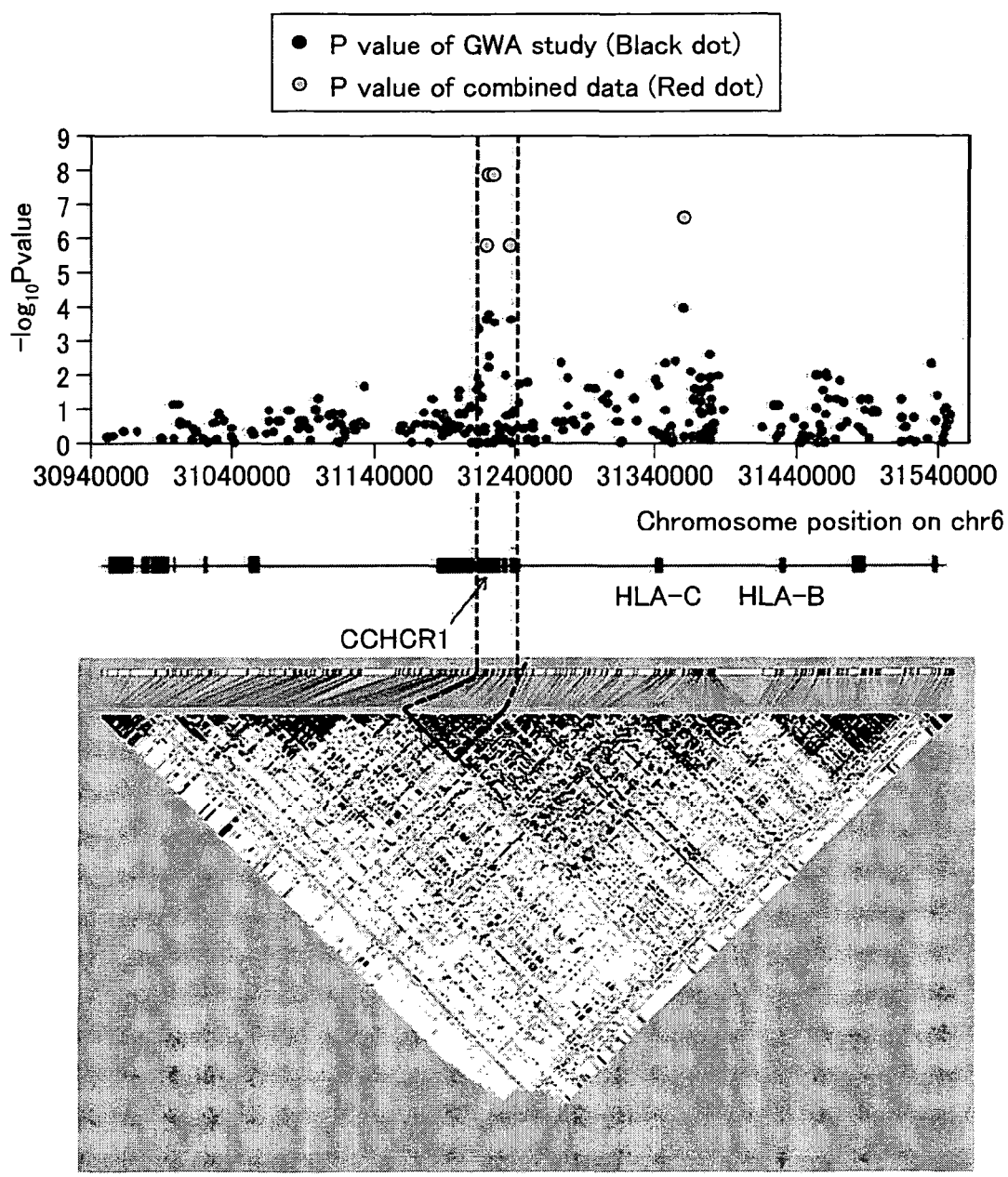
FIG. 4 is Association results of nevirapine (NVP)-induced skin rash, genomic context and linkage disequilibrium (LD) map of the CCHCR1 region on chromosome 6p21.3. Pairwise LD indices of D' from the genotype data of combined data set was drawn using Haploview's standard color scheme. Red dots represent 15 SNPs that revealed the same lowest P value ($1.2 \times 10^{-8}$).

We have further done the genotyping of all 20 tagging SNPs within this LD block based on the Han Chinese (HCB) HapMap data with $r^2>0.8$ (Table 8) and re-sequencing of the CCHCR1 gene had been carried out. Finally, we found 15 SNPs around CCHCR1 revealed significant associations with NVP-induced skin rash in That HIV patients with equivalence statistically evidence of association (FIG. 4 and Table 9). Among these 15 SNPs, rs1576, is the only non-synonymous SNP (C2783G, Ser865Cys) that has been associated with a chronic inflammatory skin disease, psoriasis in several genetic association and linkage studies. Thus, our findings strongly implicated the association of genetic variations on the CCHCR1 (Coiled-Coil α-Helical Rod protein1) gene with susceptibility to NVP-induced skin rash.

We suggest that the genetic variations in the CCHCR1 gene significantly contributes to susceptibility to NVP-induced skin rash in That population. Although the further investigations and functional studies will be need to identify the causal variant and clarify the biological mechanisms associated with NVP-induced skin rash. Our finding should shed light on the understanding of its etiology and development of diagnostic test for prevention of NVP-induced skin rash at least in Thai population.

FIG. 1 The quantile-quantile plot showing the distribution of observed statistics by allelic test for all utilized 499,730 SNPs from genome-wide association study of 72 patients with nevirapine (NVP)-induced skin rash (cases) and 77 tolerant controls. The diagonal line shows the values expected under the null hypothesis.

Figure 2:
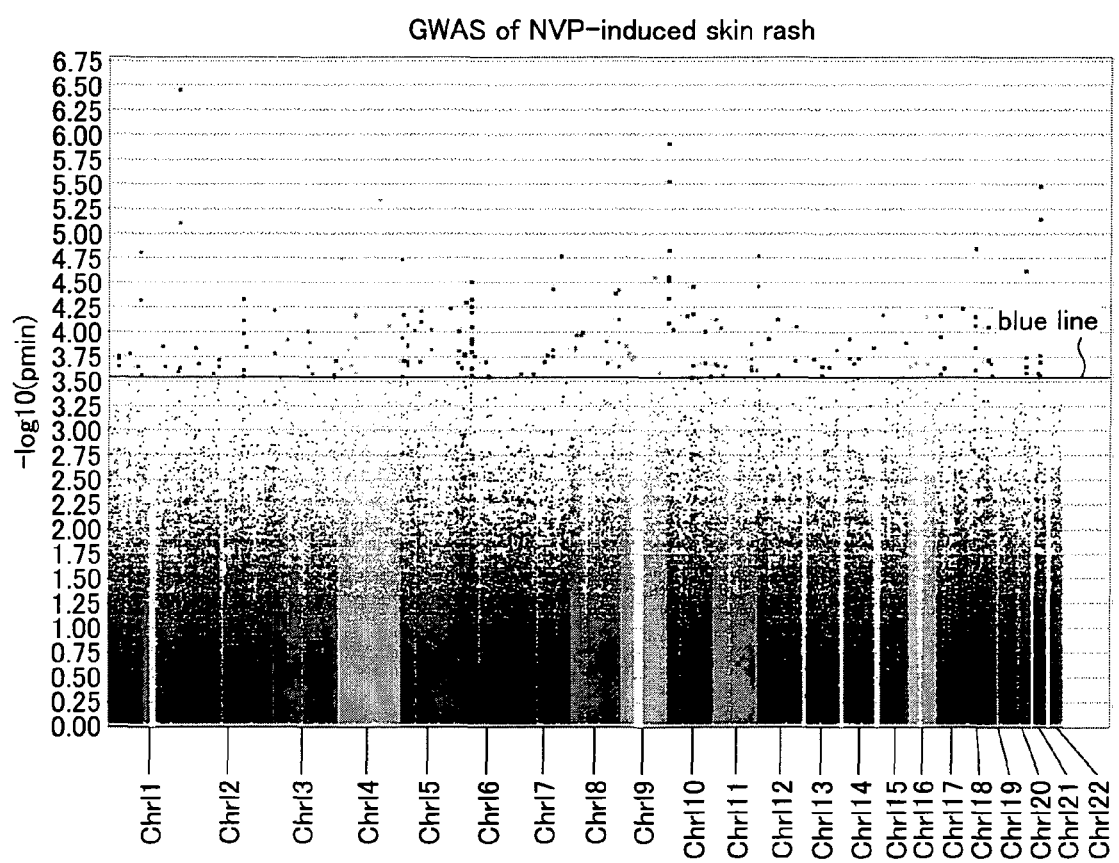
FIG. 2 is A $-\log_{10}$ P value plot from genome-wide association study. Each P value is the minimum of Fisher's exact tests for three models: allele 1 versus allele 2, genotype 11 versus 12+22 and genotype 22 versus 11+12. The blue line indicated the minimum P value of the top 200 SNPs.
Figure 3:
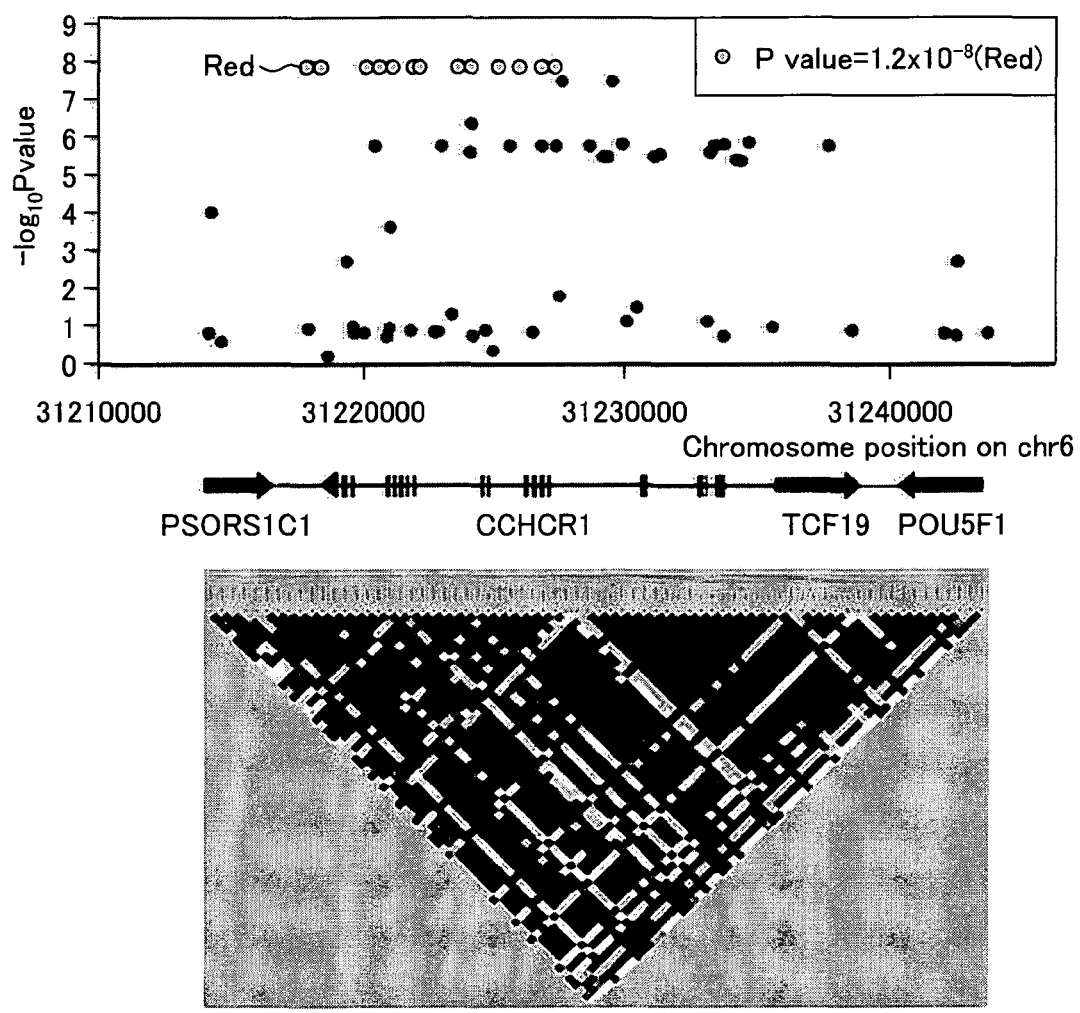
FIG. 3 is Association results of nevirapine (NVP)-induced skin rash, genomic context and linkage disequilibrium (LD) map of chromosome 6p21.3 region including the CCHCR1 locus. Pairwise LD indices of D' was drawn using Haploview's standard color scheme. Black dots and Red dots represent P values from genome-wide association study and combined data set, respectively.

FIG. 2 A $-\log_{10}$ P value plot from genome-wide association study. Each P value is the minimum of Fisher's exact tests for three models: allele 1 versus allele 2, genotype 11 versus 12+22 and genotype 22 versus 11+12. The blue line indicated the minimum P value of the top 200 SNPs.

FIG. 3 Association results of nevirapine (NVP)-induced skin rash, genomic context and linkage disequilibrium (LD) map of chromosome 6p21.3 region including the CCHCR1 locus. Pairwise LD indices of D' was drawn using Haploview's standard color scheme. Black dots and Red dots represent P values from genome-wide association study and combined data set, respectively.

FIG. 4 Association results of nevirapine (NVP)-induced skin rash, genomic context and linkage disequilibrium (LD) map of the CCHCR1 region on chromosome 6p21.3. Pairwise LD indices of D' from the genotype data of combined data set was drawn using Haploview's standard color scheme. Red dots represent 15 SNPs that revealed the same lowest P value ($1.2 \times 10^{-8}$).

TABLE 7

Results from genome-wide association study, the replication study and combined data of nevirapine-induced skin rash in Thai population.

| SNP | Chr | Gene | Alleles[a] (1/2) | Panel | Case | | | | Control | | | |
|---|---|---|---|---|---|---|---|---|---|---|---|---|
| | | | | | 11 | 12 | 22 | MAF | 11 | 12 | 22 | MAF |
| rs746647 | 6 | CCHCR1 | T/C | A | 46 | 24 | 2 | 0.194 | 69 | 8 | 0 | 0.052 |
| | | | | B | 57 | 31 | 0 | 0.176 | 128 | 15 | 2 | 0.066 |
| | | | | Combined | 103 | 55 | 2 | 0.184 | 197 | 23 | 2 | 0.061 |
| rs1265112 | 6 | CCHCR1 | A/G | A | 46 | 24 | 2 | 0.194 | 68 | 8 | 0 | 0.053 |
| | | | | B | 57 | 31 | 0 | 0.176 | 128 | 15 | 2 | 0.066 |
| | | | | Combined | 103 | 55 | 2 | 0.184 | 197 | 23 | 2 | 0.061 |
| rs9461684 | 6 | 13 kb near 3' end of HLA-C | C/T | A | 51 | 20 | 1 | 0.153 | 73 | 4 | 0 | 0.026 |
| | | | | B | 70 | 18 | 0 | 0.102 | 136 | 9 | 0 | 0.031 |
| | | | | Combined | 121 | 38 | 1 | 0.125 | 209 | 13 | 0 | 0.029 |
| rs130072 | 6 | CCHCR1 | G/A | A | 52 | 19 | 1 | 0.146 | 73 | 4 | 0 | 0.026 |
| | | | | B | 73 | 15 | 0 | 0.085 | 137 | 8 | 0 | 0.028 |
| | | | | Combined | 125 | 34 | 1 | 0.113 | 210 | 12 | 0 | 0.027 |
| rs2073724 | 6 | TCF19 | C/T | A | 52 | 19 | 1 | 0.146 | 73 | 4 | 0 | 0.026 |
| | | | | B | 73 | 15 | 0 | 0.085 | 137 | 8 | 0 | 0.028 |
| | | | | Combined | 125 | 34 | 1 | 0.113 | 210 | 12 | 0 | 0.027 |
| rs6545803 | 2 | Intergene | G/T | A | 40 | 25 | 7 | 0.271 | 20 | 44 | 13 | 0.455 |
| | | | | B | 39 | 39 | 10 | 0.335 | 39 | 82 | 24 | 0.448 |
| | | | | Combined | 79 | 64 | 17 | 0.306 | 59 | 126 | 37 | 0.450 |

TABLE 7-continued

Results from genome-wide association study, the replication study and combined data of nevirapine-induced skin rash in Thai population.

| | | | | | | | | | | | | |
|---|---|---|---|---|---|---|---|---|---|---|---|---|
| rs2562519 | 5 | POLR3G | A/G | A | 36 | 30 | 6 | 0.292 | 17 | 41 | 19 | 0.487 |
| | | | | B | 40 | 38 | 10 | 0.330 | 47 | 63 | 35 | 0.459 |
| | | | | Combined | 76 | 68 | 16 | 0.313 | 64 | 104 | 54 | 0.477 |

| | | P value (Fisher's exact test) | | | |
|---|---|---|---|---|---|
| SNP | Risk allele | Allele 1 versus allele 2 | Genotype 11 versus 12 + 22 | Genotype 11 + 12 versus 22 | Minimum |
| rs746647 | C | 1.6E−04 | 1.9E−04 | 2.3E−01 | 1.6E−04 |
| | | 2.3E−04 | 2.6E−05 | 5.3E−01 | 2.6E−05 |
| | | 1.2E−07 | 1.2E−08 | 1.0E+00 | 1.2E−08 |
| rs1265112 | G | 2.7E−04 | 3.4E−04 | 2.3E−01 | 2.7E−04 |
| | | 2.3E−04 | 2.6E−05 | 5.3E−01 | 2.6E−05 |
| | | 1.2E−07 | 1.2E−08 | 1.0E+00 | 1.2E−08 |
| rs9461684 | T | 1.2E−04 | 1.1E−04 | 4.8E−01 | 1.1E−04 |
| | | 2.0E−03 | 1.4E−03 | 1.0E+00 | 1.4E−03 |
| | | 3.0E−07 | 2.1E−07 | 4.2E−01 | 2.1E−07 |
| rs130072 | A | 2.3E−04 | 2.3E−04 | 4.8E−01 | 2.3E−04 |
| | | 7.4E−03 | 6.0E−03 | 1.0E+00 | 6.0E−03 |
| | | 1.8E−06 | 1.5E−06 | 4.2E−01 | 1.5E−06 |
| rs2073724 | T | 2.3E−04 | 2.3E−04 | 4.8E−01 | 2.3E−04 |
| | | 7.4E−03 | 6.0E−03 | 1.0E+00 | 6.0E−03 |
| | | 1.8E−06 | 1.5E−06 | 4.2E−01 | 1.5E−06 |
| rs6545803 | G | 1.1E−03 | 2.6E−04 | 2.4E−01 | 2.6E−04 |
| | | 1.9E−02 | 6.9E−03 | 3.4E−01 | 6.9E−03 |
| | | 6.5E−05 | 5.6E−06 | 1.0E−01 | 5.6E−06 |
| rs2562519 | A | 5.6E−04 | 8.6E−03 | 1.5E−04 | 1.5E−04 |
| | | 5.1E−02 | 2.5E−02 | 6.6E−03 | 6.6E−03 |
| | | 2.4E−04 | 4.3E−04 | 5.1E−06 | 5.1E−06 |

[a]Major allele in controls was defined as allele 1.

Chr; Chromosome, MAF; minor allele frequency

TABLE 8

Association results of 20 tagging SNPs within the linkage disequilibrium (LD) block of the susceptible region (Chr6: 31214000 . . . 31243800).

| | | | Alleles[a] | Case | | | | Control | | | |
|---|---|---|---|---|---|---|---|---|---|---|---|
| SNP | Chr position | Gene | (1/2) | 11 | 12 | 22 | MAF | 11 | 12 | 22 | MAF |
| rs1265098 | 31214156 | PSORS1 | T > C | 122 | 37 | 0 | 0.116 | 166 | 52 | 4 | 0.135 |
| rs3130573 | 31214247 | PSORS1 | A > G | 77 | 63 | 20 | 0.322 | 142 | 73 | 7 | 0.196 |
| rs1265095 | 31214622 | PSORS1 | A > G | 52 | 70 | 36 | 0.449 | 62 | 101 | 59 | 0.493 |
| rs1265085 | 31218650 | CCHCR1 | G > C | 62 | 81 | 16 | 0.355 | 83 | 121 | 18 | 0.354 |
| rs9263740 | 31219379 | CCHCR1 | T > C | 100 | 49 | 11 | 0.222 | 102 | 107 | 13 | 0.300 |
| rs1265080 | 31220054 | CCHCR1 | G > A | 54 | 83 | 23 | 0.403 | 83 | 119 | 20 | 0.358 |
| rs1265079 | 31220087 | CCHCR1 | C > A | 103 | 55 | 2 | 0.184 | 197 | 23 | 2 | 0.061 |
| rs2073719 | 31220904 | CCHCR1 | A > G | 94 | 59 | 7 | 0.228 | 115 | 93 | 14 | 0.273 |
| rs3094225 | 31221031 | CCHCR1 | T > C | 67 | 72 | 21 | 0.356 | 53 | 128 | 41 | 0.473 |
| rs3132538 | 31221821 | CCHCR1 | C > T | 122 | 37 | 1 | 0.122 | 153 | 65 | 4 | 0.164 |
| rs130068 | 31224225 | CCHCR1 | G > A | 58 | 75 | 26 | 0.399 | 87 | 110 | 25 | 0.360 |
| rs130078 | 31226544 | CCHCR1 | G > C | 91 | 62 | 7 | 0.238 | 110 | 97 | 15 | 0.286 |
| rs1265109 | 31227568 | CCHCR1 | T > G | 34 | 85 | 41 | 0.478 | 73 | 98 | 51 | 0.450 |
| rs130065 | 31230479 | CCHCR1 | C > T | 139 | 21 | 0 | 0.066 | 208 | 13 | 1 | 0.034 |
| rs720465 | 31233756 | 5' to CCHCR1 | C > A | 117 | 39 | 3 | 0.142 | 177 | 39 | 6 | 0.115 |
| rs6905862 | 31235581 | TCF19 | G > A | 52 | 80 | 28 | 0.425 | 76 | 121 | 25 | 0.385 |
| rs1419881 | 31238572 | 3' to POU5F1 | T > C | 44 | 88 | 28 | 0.450 | 78 | 104 | 40 | 0.414 |
| rs1265163 | 31242066 | POU5F1 | C > G | 80 | 61 | 14 | 0.287 | 112 | 95 | 11 | 0.268 |
| rs3757349 | 31242511 | POU5F1 | A > G | 130 | 26 | 4 | 0.106 | 179 | 42 | 1 | 0.099 |
| rs11965454 | 31242570 | POU5F1 | A > G | 123 | 33 | 4 | 0.128 | 137 | 77 | 8 | 0.209 |
| rs9263805 | 31243714 | POU5F1 | G > T | 90 | 52 | 17 | 0.270 | 108 | 95 | 19 | 0.300 |

TABLE 8-continued

Association results of 20 tagging SNPs within the linkage disequilibrium
(LD) block of the susceptible region (Chr6: 31214000 . . . 31243800).

|  |  | P value (Fisher's exact test) |  |  |  |
| --- | --- | --- | --- | --- | --- |
| SNP | Risk allele | Allele 1 versus allele 2 | Genotype 11 versus 12 + 22 | Genotype 11 + 12 versus 22 | Minimum |
| rs1265098 | T | 5.1E−01 | 7.2E−01 | 1.4E−01 | 1.4E−01 |
| rs3130573 | G | 9.1E−05 | 2.4E−03 | 5.2E−04 | 9.1E−05 |
| rs1265095 | A | 2.4E−01 | 3.1E−01 | 4.7E−01 | 2.4E−01 |
| rs1265085 | C | 1.0E+00 | 8.3E−01 | 5.9E−01 | 5.9E−01 |
| rs9263740 | T | 2.0E−02 | 1.8E−03 | 8.3E−01 | 1.8E−03 |
| rs1265080 | A | 2.3E−01 | 5.2E−01 | 1.4E−01 | 1.4E−01 |
| rs1265079 | A | 1.2E−07 | 1.2E−08 | 1.0E+00 | 1.2E−08 |
| rs2073719 | A | 1.8E−01 | 2.1E−01 | 5.0E−01 | 1.8E−01 |
| rs3094225 | T | 1.4E−03 | 2.2E−04 | 2.1E−01 | 2.2E−04 |
| rs3132538 | C | 1.2E−01 | 1.3E−01 | 4.0E−01 | 1.2E−01 |
| rs130068 | A | 2.9E−01 | 5.9E−01 | 1.7E−01 | 1.7E−01 |
| rs130078 | G | 1.4E−01 | 1.8E−01 | 3.8E−01 | 1.4E−01 |
| rs1265109 | G | 5.6E−02 | 1.5E−02 | 6.3E−01 | 1.5E−02 |
| rs130065 | T | 5.6E−02 | 3.0E−02 | 1.0E+00 | 3.0E−02 |
| rs720465 | A | 3.2E−01 | 1.7E−01 | 7.4E−01 | 1.7E−01 |
| rs6905862 | A | 3.0E−01 | 7.4E−01 | 9.9E−02 | 9.9E−02 |
| rs1419881 | C | 3.4E−01 | 1.2E−01 | 1.0E+00 | 1.2E−01 |
| rs1265163 | G | 6.2E−01 | 1.0E+00 | 1.4E−01 | 1.4E−01 |
| rs3757349 | G | 8.1E−01 | 9.0E−01 | 1.7E−01 | 1.7E−01 |
| rs11965454 | A | 3.8E−03 | 1.8E−03 | 5.7E−01 | 1.8E−03 |
| rs9263805 | G | 4.2E−01 | 1.5E−01 | 5.9E−01 | 1.5E−01 |

[a] Major allele in controls was defined as allele 1.
MAF; minor allele frequency

TABLE 9

Risk of nevirapine-induced skin rash associated with 15 SNPs in CCHCR1 region

|  |  |  |  | Case |  |  |  | Control |  |  |  |  | P value (Fisher's exact test) |  |  |  |
| --- | --- | --- | --- | --- | --- | --- | --- | --- | --- | --- | --- | --- | --- | --- | --- | --- |
| SNP | Alleles[a] (1/2) | Amino acid change | Location in CCHCR1 | 11 | 12 | 22 | MAF | 11 | 12 | 22 | MAF | Risk allele | Allele 1 versus allele 2 | Genotype 11 versus 12 + 22 | Genotype 11 + 12 versus 22 | Minimum |
| rs1265111 | C > T |  | intron 4 | 103 | 55 | 2 | 0.184 | 197 | 23 | 2 | 0.061 | T | 1.2E−08 | 1.0E+00 | 1.2E−07 | 1.2E−08 |
| rs2517985 | A > G |  | intron 4 | 103 | 55 | 2 | 0.184 | 197 | 23 | 2 | 0.061 | G | 1.2E−08 | 1.0E+00 | 1.2E−07 | 1.2E−08 |
| rs1265112 | A > G |  | Intron 7 | 103 | 55 | 2 | 0.184 | 197 | 23 | 2 | 0.061 | G | 1.2E−08 | 1.0E+00 | 1.2E−07 | 1.2E−08 |
| rs1265114 | C > T |  | Intron 8 | 103 | 55 | 2 | 0.184 | 197 | 23 | 2 | 0.061 | T | 1.2E−08 | 1.0E+00 | 1.2E−07 | 1.2E−08 |
| rs1265069 | T > C |  | Intron 10 | 103 | 55 | 2 | 0.184 | 197 | 23 | 2 | 0.061 | C | 1.2E−08 | 1.0E+00 | 1.2E−07 | 1.2E−08 |
| rs1265067 | C > T |  | Intron 10 | 103 | 55 | 2 | 0.184 | 197 | 23 | 2 | 0.061 | T | 1.2E−08 | 1.0E+00 | 1.2E−07 | 1.2E−08 |
| rs746647 | T > C |  | Intron 10 | 103 | 55 | 2 | 0.184 | 197 | 23 | 2 | 0.061 | C | 1.2E−08 | 1.0E+00 | 1.2E−07 | 1.2E−08 |
| rs746646 | A > G |  | Intron 10 | 103 | 55 | 2 | 0.184 | 197 | 23 | 2 | 0.061 | G | 1.2E−08 | 1.0E+00 | 1.2E−07 | 1.2E−08 |
| rs1265076 | C > T |  | Intron 12 | 103 | 55 | 2 | 0.184 | 197 | 23 | 2 | 0.061 | T | 1.2E−08 | 1.0E+00 | 1.2E−07 | 1.2E−08 |
| rs1265078 | C > G |  | Intron 14 | 103 | 55 | 2 | 0.184 | 197 | 23 | 2 | 0.061 | G | 1.2E−08 | 1.0E+00 | 1.2E−07 | 1.2E−08 |
| rs1265079 | C > A |  | Intron 15 | 103 | 55 | 2 | 0.184 | 197 | 23 | 2 | 0.061 | A | 1.2E−08 | 1.0E+00 | 1.2E−07 | 1.2E−08 |
| rs1576 | C > G | Ser > Cys | exon 18 | 103 | 55 | 2 | 0.184 | 197 | 23 | 2 | 0.061 | G | 1.2E−08 | 1.0E+00 | 1.2E−07 | 1.2E−08 |
| rs2523833 | G > A |  | 3' UTR | 103 | 55 | 2 | 0.184 | 197 | 23 | 2 | 0.061 | A | 1.2E−08 | 1.0E+00 | 1.2E−07 | 1.2E−08 |
| rs2523834 | A > T |  | 3' UTR | 103 | 55 | 2 | 0.184 | 197 | 23 | 2 | 0.061 | T | 1.2E−08 | 1.0E+00 | 1.2E−07 | 1.2E−08 |
| rs1265087 | C > T |  | 3' UTR | 103 | 55 | 2 | 0.184 | 197 | 23 | 2 | 0.061 | T | 1.2E−08 | 1.0E+00 | 1.2E−07 | 1.2E−08 |

[a] Major allele in controls was defined as allele 1.
MAF; minor allele frequency

The invention claimed is:

1. A method of assessing the risk of an HIV-infected patient for developing a cutaneous adverse reaction to nevirapine and treating the HIV-infected patient, comprising:

assessing the risk of the HIV-infected patient for developing a cutaneous adverse reaction to nevirapine by genotyping a sample obtained from the HIV-infected patient at the rs1576 single nucleotide polymorphism (SNP) locus in the CCHCR1 gene, wherein the presence of a homozygous C/C allele at the rs1576 SNP locus is indicative of no risk allele for the cutaneous adverse drug reaction to nevirapine, and administering nevirapine to the HIV-infected patient if the genotyped rs1576 SNP indicates the presence of a homozygous C/C allele at the rs1576 SNP locus, administering an antiretroviral drug therapy not including nevirapine to the HIV-infected patient if the genotyped rs1576 SNP indicates the presence of a C/G or G/G allele at the rs1576 SNP locus.

2. The method according to claim 1, wherein the cutaneous adverse reaction is comprising of maculopapular, erythema multiforme (EM), urticaria angioedema, fixed drug eruption, Steven-Jonhson syndrome (SJS) or Toxic Epidermal Necrosis (TEN).

3. The method according to claim 1, wherein the sample obtained from the HIV-infected patient is derived from the peripheral blood of the HIV-infected patient.

4. The method according to claim 3, wherein the sample obtained from the HIV-infected patient is DNA, RNA, protein, or cells prepared from the peripheral blood of the HIV-infected patient.

* * * * *